(12) United States Patent
Borglin et al.

(10) Patent No.: US 10,939,990 B2
(45) Date of Patent: Mar. 9, 2021

(54) GRAFT MATERIAL HAVING SELECTIVELY ADVANCED PERMEABILITY STRUCTURE AND METHOD

(71) Applicant: Medtronic Vascular, Inc., Santa Rosa, CA (US)

(72) Inventors: Zachary Borglin, Santa Rosa, CA (US); Matt Petruska, Santa Rosa, CA (US); Keith Perkins, Santa Rosa, CA (US); Julie Benton, Santa Rosa, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 71 days.

(21) Appl. No.: 15/950,612

(22) Filed: Apr. 11, 2018

(65) Prior Publication Data

US 2019/0159881 A1 May 30, 2019

Related U.S. Application Data

(60) Provisional application No. 62/591,601, filed on Nov. 28, 2017.

(51) Int. Cl.
*A61F 2/07* (2013.01)
*D02G 3/36* (2006.01)
(Continued)

(52) U.S. Cl.
CPC .............. *A61F 2/07* (2013.01); *A61F 2/0077* (2013.01); *A61F 2/06* (2013.01); *A61L 27/18* (2013.01);
(Continued)

(58) Field of Classification Search
None
See application file for complete search history.

(56) References Cited

U.S. PATENT DOCUMENTS 5,744,515 A * 4/1998 Clapper ................. A61L 27/16
424/423
5,769,884 A * 6/1998 Solovay ..................... A61F 2/07
606/194

(Continued)

FOREIGN PATENT DOCUMENTS

DE        3546875 C2     5/1996
DE    102014110013 A1    1/2016
(Continued)

OTHER PUBLICATIONS

Translation of DE102014110013A1 retrieved from espacenet on Apr. 2, 2020 (Year: 2020).*

(Continued)

*Primary Examiner* — Megan Y Wolf
(74) *Attorney, Agent, or Firm* — Innovation Counsel LLP

(57) ABSTRACT

A laser is used to form openings within a graft material to selectively enhance permeability of a prosthesis for tissue integration therein. A feature of utilizing a laser to create the openings for tissue integration builds from its tunability. More particularly, the laser precisely places openings in any pattern and location, and on any textile that forms the graft material. Further, the power and focus of the laser is precisely adjusted to control the diameter and shape of the openings. All parameters of the openings can be controlled at will, allowing for the opportunity to selectively enhance and optimize the permeability of the graft material in a vessel.

12 Claims, 11 Drawing Sheets

(51) Int. Cl.

| | |
|---|---|
| *A61L 27/58* | (2006.01) |
| *D03D 1/00* | (2006.01) |
| *D03D 15/00* | (2021.01) |
| *A61F 2/06* | (2013.01) |
| *D02G 3/44* | (2006.01) |
| *A61F 2/00* | (2006.01) |
| *A61L 27/18* | (2006.01) |
| *A61L 27/54* | (2006.01) |
| *A61L 27/56* | (2006.01) |
| *A61L 31/14* | (2006.01) |
| *A61L 31/16* | (2006.01) |
| *A61L 31/02* | (2006.01) |
| *A61L 31/06* | (2006.01) |
| *A61L 31/10* | (2006.01) |
| *B23K 26/388* | (2014.01) |
| *A61L 31/04* | (2006.01) |

(52) U.S. Cl.
CPC ............. *A61L 27/54* (2013.01); *A61L 27/56* (2013.01); *A61L 27/58* (2013.01); *A61L 31/022* (2013.01); *A61L 31/06* (2013.01); *A61L 31/10* (2013.01); *A61L 31/148* (2013.01); *A61L 31/16* (2013.01); *D02G 3/36* (2013.01); *D02G 3/448* (2013.01); *D03D 1/00* (2013.01); *D03D 15/0027* (2013.01); *D03D 15/0094* (2013.01); *A61F 2002/0081* (2013.01); *A61F 2002/065* (2013.01); *A61F 2002/075* (2013.01); *A61F 2002/077* (2013.01); *A61F 2210/0004* (2013.01); *A61F 2210/0014* (2013.01); *A61F 2210/0057* (2013.01); *A61F 2210/0071* (2013.01); *A61F 2210/0076* (2013.01); *A61F 2220/0075* (2013.01); *A61F 2230/0069* (2013.01); *A61F 2240/001* (2013.01); *A61F 2250/0003* (2013.01); *A61F 2250/003* (2013.01); *A61F 2250/0023* (2013.01); *A61F 2250/0024* (2013.01); *A61F 2250/0031* (2013.01); *A61F 2250/0051* (2013.01); *A61F 2250/0067* (2013.01); *A61F 2250/0068* (2013.01); *A61F 2250/0069* (2013.01); *A61F 2250/0076* (2013.01); *A61L 31/043* (2013.01); *A61L 2300/258* (2013.01); *A61L 2300/404* (2013.01); *A61L 2300/41* (2013.01); *A61L 2300/412* (2013.01); *A61L 2300/42* (2013.01); *A61L 2420/02* (2013.01); *A61L 2420/08* (2013.01); *B23K 26/388* (2013.01); *D10B 2101/20* (2013.01); *D10B 2331/04* (2013.01); *D10B 2509/06* (2013.01)

(56) References Cited

U.S. PATENT DOCUMENTS

| | | | | |
|---|---|---|---|---|
| 5,976,178 A * | 11/1999 | Goldsteen | ............ | A61B 1/0058 128/898 |
| 6,074,416 A * | 6/2000 | Berg | ........................ | A61F 2/064 623/1.36 |
| 6,278,079 B1 * | 8/2001 | McIntyre | .................. | A61F 2/07 219/121.67 |
| 6,371,982 B2 * | 4/2002 | Berg | ........................ | A61F 2/06 623/1.13 |
| 9,486,346 B2 | 11/2016 | Argentine | | |
| 2002/0035394 A1 * | 3/2002 | Fierens | ..................... | A61F 2/07 623/1.13 |
| 2005/0131516 A1 * | 6/2005 | Greenhalgh | .............. | A61F 2/07 623/1.13 |
| 2005/0186241 A1 * | 8/2005 | Boyle | .................... | A61B 5/076 424/423 |
| 2005/0220848 A1 | 10/2005 | Bates | | |
| 2007/0282160 A1 | 12/2007 | Sheu et al. | | |
| 2008/0188923 A1 | 8/2008 | Chu | | |
| 2009/0043330 A1 | 2/2009 | To | | |
| 2013/0261732 A1 * | 10/2013 | Perkins | ..................... | A61F 2/07 623/1.15 |
| 2013/0267137 A1 | 10/2013 | Peniston et al. | | |
| 2016/0158038 A1 * | 6/2016 | Teitelbaum | ............... | A61F 2/90 623/1.11 |
| 2017/0231749 A1 | 8/2017 | Perkins et al. | | |
| 2017/0360993 A1 | 12/2017 | Argentine et al. | | |

FOREIGN PATENT DOCUMENTS

| | | |
|---|---|---|
| EP | 0144534 A2 | 6/1985 |
| EP | 0397500 B1 | 2/1995 |
| EP | 1820889 B1 | 3/2009 |
| WO | 2000047135 A1 | 8/2000 |
| WO | 2004037116 A2 | 5/2004 |
| WO | 2011103141 A1 | 8/2011 |
| WO | 2013097841 A1 | 7/2013 |
| WO | 2013128718 A1 | 9/2013 |
| WO | 2014133798 A1 | 9/2014 |
| WO | 2017079659 A1 | 11/2016 |

OTHER PUBLICATIONS

U.S. Appl. No. 62/591,601, titled "Advanced Graft Materials for Endovascular Applications", filed Nov. 28, 2017.
U.S. Appl. No. 16/142,545, titled "Armored Graft Material Structure and Method", filed Sep. 26, 2018.
U.S. Appl. No. 16/143,932, titled "Graft Material Having Heated Puncture Structure and Method", filed Sep. 27, 2018.
U.S. Appl. No. 16/144,078, titled "Biodegradable Composite Yarn Structure and Method", filed Sep. 27, 2018.
U.S. Appl. No. 16/143,125, titled "Framed Biodegradable Yarn Structure and Method", filed Sep. 26, 2018.
U.S. Appl. No. 16/156,271, titled "Variable Permeability Layered Structure and Method", filed Oct. 10, 2018.
PCT/US2018/062482, The International Search Report and the Written Opinion of the Int'l Searching Authority, dated Mar. 27, 2019, 14 pages.
PCT/US2018/062512, The International Search Report and the Written Opinion of the Int'l Searching Authority, dated Apr. 17, 2019, 12 pages.
PCT/US2018/062516, The International Search Report and the Written Opinion of the Int'l Searching Authority, dated Mar. 27, 2019, 13 pages.
PCT/US2018/062549, The International Search Report and the Written Opinion of the Int'l Searching Authority, dated Mar. 28, 2019, 13 pages.
PCT/US2018/062581, The International Search Report and the Written Opinion of the Int'l Searching Authority, dated Mar. 27, 2019, 15 pages.
PCT/US2018/062589, The International Search Report and the Written Opinion of the Int'l Searching Authority, dated Mar. 27, 2019, 13 pages.

* cited by examiner

Single shot

Percussion

Trepanning

Helical

ABSTRACT# GRAFT MATERIAL HAVING SELECTIVELY ADVANCED PERMEABILITY STRUCTURE AND METHOD

RELATED APPLICATIONS

This application claims the benefit of U.S. Provisional Application No. 62/591,601, filed on Nov. 28, 2017, entitled "ADVANCED GRAFT MATERIALS FOR ENDOVASCULAR APPLICATIONS" of Borglin et al., which is incorporated herein by reference in its entirety.

BACKGROUND

Field

The present application relates to an intra-vascular device and method. More particularly, the present application relates to a device for treatment of intra-vascular diseases.

Description of the Related Art

A conventional stent-graft typically includes a radially expandable reinforcement structure, formed from a plurality of annular stent rings, and a cylindrically shaped layer of graft material defining a lumen to which the stent rings are coupled. Stent-grafts are well known for use in tubular shaped human vessels.

To illustrate, endovascular aneurysmal exclusion is a method of using a stent-graft to exclude pressurized fluid flow from the interior of an aneurysm, thereby reducing the risk of rupture of the aneurysm and the associated invasive surgical intervention.

The graft material of traditional stent-grafts is extremely hydrophobic and presents a hostile environment for the recruitment and proliferation of cells. The inability of tissue to integrate into the graft material prevents the biological fixation of the stent-graft in vessels and makes the stent-graft susceptible to endoleaks and migration.

SUMMARY

A laser is used to form openings within a graft material to selectively enhance permeability of a prosthesis for tissue integration therein. A feature of utilizing a laser to create the openings for tissue integration builds from its tunability. More particularly, the laser precisely places openings in any pattern and location, and on any textile that forms the graft material. Further, the power and focus of the laser is precisely adjusted to control the diameter and shape of the openings. All parameters of the openings can be controlled at will, allowing for the opportunity to selectively enhance and optimize the permeability of the graft material in a vessel.

In one embodiment, the openings are filled with a bioactive material to encourage tissue growth therein.

Embodiments are best understood by reference to the following detailed description when read in conjunction with the accompanying drawings.

BRIEF DESCRIPTION OF DRAWINGS

Common reference numerals are used throughout the drawings and detailed description to indicate like elements.

DETAILED DESCRIPTION

Figure 1:
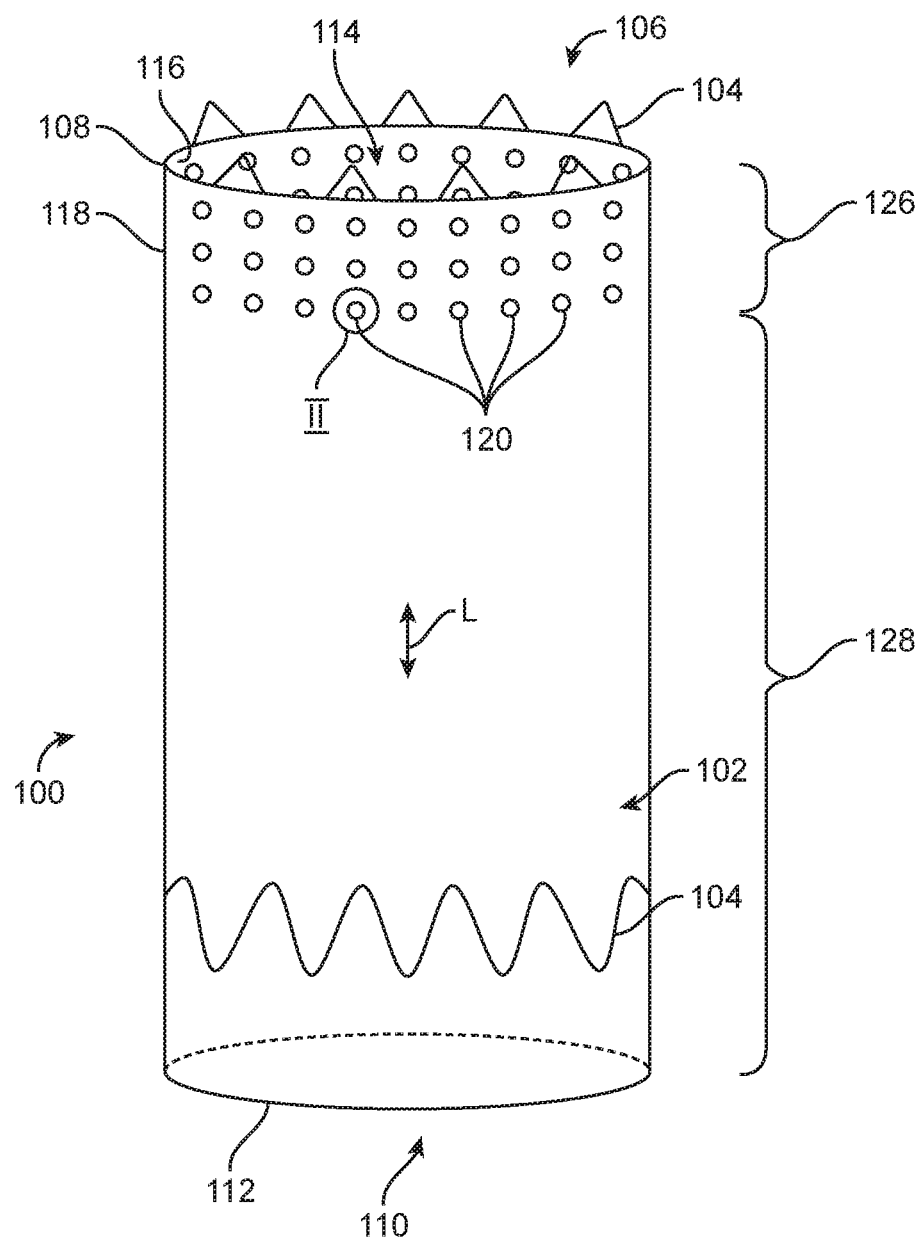
FIG. 1 is a perspective view of a selectively enhanced permeability stent-graft in accordance with one embodiment.

As an overview and in accordance with one embodiment, referring to FIG. 1, a laser is used to form openings 120 within a graft material 102 to selectively enhance permeability of a stent-graft 100 for tissue integration therein. A feature of utilizing a laser to create openings 120 for tissue integration builds from its tunability. More particularly, the laser in accordance with one embodiment precisely places openings 120 in any pattern and location, and on any textile that forms graft material 102. Further, the power and focus of the laser is precisely adjusted to control the diameter and shape of openings 120. All parameters of openings 120 can be controlled at will, allowing for the opportunity to selectively enhance and optimize the permeability of graft material 102 in a vessel.

Now in more detail, FIG. 1 is a perspective view of a selectively enhanced permeability stent-graft 100, e.g., an abdominal aortic stent-graft, in accordance with one embodiment. Referring now to FIG. 1, stent-graft 100, sometimes called a prosthesis, includes a selectively enhanced permeability graft material 102 and one or more stent rings 104. Illustratively, stent rings 104 are self-expanding stent rings, e.g., nickel titanium alloy (NiTi), sometimes called Nitinol. The inclusion of stent rings 104 is optional and in one embodiment stent rings 104 are not included.

In accordance with this embodiment, graft material 102, sometimes called a textile, includes a proximal opening 106 at a proximal end 108 of graft material 102 and a distal opening 110 at a distal end 112 of graft material 102.

Further, stent-graft 100 includes a longitudinal axis L. A lumen 114 is defined by graft material 102, and generally by stent-graft 100. Lumen 114 extends generally parallel to longitudinal axis L and between proximal opening 106 and distal opening 110 of stent-graft 100.

As used herein, the proximal end of a prosthesis such as stent-graft 100 is the end closest to the heart via the path of blood flow whereas the distal end is the end furthest away from the heart during deployment. In contrast and of note, the distal end of the catheter is usually identified to the end that is farthest from the operator (handle) while the proximal end of the catheter is the end nearest the operator (handle).

For purposes of clarity of discussion, as used herein, the distal end of the catheter is the end that is farthest from the operator (the end furthest from the handle) while the distal end of stent-graft 100 is the end nearest the operator (the end nearest the handle), i.e., the distal end of the catheter and the proximal end of stent-graft 100 are the ends furthest from the handle while the proximal end of the catheter and the distal end of stent-graft 100 are the ends nearest the handle. However, those of skill in the art will understand that depending upon the access location, stent-graft 100 and the delivery system descriptions may be consistent or opposite in actual usage.

Graft material 102 is cylindrical having a substantially uniform diameter. However, in other embodiments, graft material 102 varies in diameter and/or is bifurcated at distal end 112. Graft material 102 includes an inner surface 116 and an opposite outer surface 118, e.g., cylindrical surfaces.

In one embodiment, graft material 102 is hydrophobic, e.g., is polyester terephthalate (PET), expanded polyester terephthalate (ePET), or other graft material or textile. As graft material 102 is hydrophobic, graft material 102 in itself presents a hostile environment for the recruitment and the proliferation of cells. However, in accordance with this embodiment, the permeability of graft material 102 is selectively enhance to encourage tissue integration therein.

Figure 2:
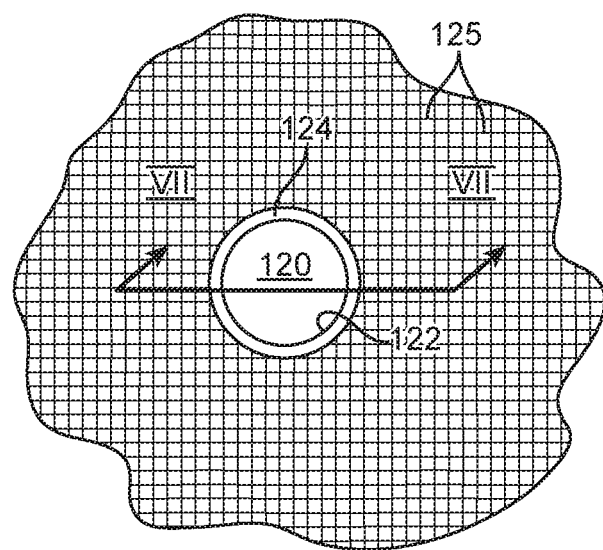
FIG. 2 is an enlarged plan view of a region II of a graft material of the stent-graft of FIG. 1 in accordance with one embodiment.

FIG. 2 is an enlarged plan view of a region II of graft material 102 of stent-graft 100 of FIG. 1 in accordance with one embodiment. Referring now to FIGS. 1 and 2 together, a plurality of openings 120 are formed within graft material 102, a single opening 120 being illustrated in FIG. 2. Openings 120 extends entirely through graft material 102 and between inner surface 116 and outer surface 118.

In accordance with this embodiment, openings 120 are circular and include a circumference 122, e.g., an edge of graft material 102 that defines openings 120. In one embodiment, the diameter of openings 120 is within the approximate range of 20-250 microns. However, in other embodiments, openings 120 have a diameter greater than 250 microns depending upon the particular application.

Extending outward from circumference 122 is a fused region 124. Fused region 124 is an area of graft material 102 that has been fused together. For example, openings 120 are formed using a laser. Openings 120 are sometimes called laser-created openings 120. During formation of openings 120, the laser melts fused region 124, which then cools to form a solid fused region 124. In other words, fused region 124 is a region which has been melted and fused together.

In accordance with this embodiment, fused region 124 is shaped as an annulus around opening 120, i.e., extending outward from circumference 122. However, in other embodiments, openings 120 are noncircular shapes, e.g., are linear, oval, conical, or other shapes. Generally, fused region 124 is an area, e.g., a continuous strip, extending outward from and surrounding opening 120.

By forming fused region 124, openings 120 produced by a laser have an inherent resistance to textile wear as the filaments 125 along the edge, e.g., circumference 122, of each opening 120 are bonded together by the heat of the laser. This produces a stable textile, e.g., graft material 102, with openings 120 that can be supplemented with bioactive material as discussed further below. In one embodiment, graft material 102 is formed of filaments 125 weaved or otherwise combined together.

Figure 3:
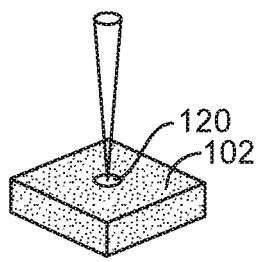
FIG. 3 is a perspective view of the formation of an opening using a single shot laser in accordance with one embodiment.

FIG. 3 is a perspective view of the formation of opening 120 using a single shot laser in accordance with one embodiment. In accordance with this embodiment, a single shot from a laser is directed at graft material 102 to form opening 120. The laser is then moved and the single shot is repeated any one of a number of times depending upon the particular numbers of openings 120 to be formed. The single shot from the laser is also called pulsed laser drilling.

Figure 4:
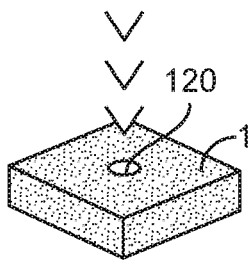
FIG. 4 is a perspective view of the formation of an opening using a percussion laser in accordance with one embodiment.

FIG. 4 is a perspective view of the formation of opening 120 using a percussion laser in accordance with one embodiment. In accordance with this embodiment, a plurality of shots from a laser are directed at graft material 102 to form opening 120. The plurality of shots are aimed at the same location as to form a single opening 120. The plurality of shots at the same location without relative movement of graft material 102 and the laser is sometimes called percussion laser beam drilling. The laser is then moved and the percussion laser beam drilling is repeated any one of a number of times depending upon the particular numbers of openings 120 to be formed.

Figure 5:
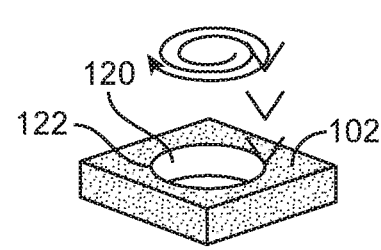
FIG. 5 is a perspective view of the formation of an opening using a trepanning laser in accordance with one embodiment.

FIG. 5 is a perspective view of the formation of opening 120 using a trepanning laser in accordance with one embodiment. In accordance with this embodiment, a continuous laser shot is moved, e.g., in an increasing spiral, at graft material 102 to form opening 120. For example, the laser initially pierces a hole in the middle of opening 120 and then moves in a spiral to form a single opening 120. The spiral motion of the laser is sometimes called trepanning laser beam drilling. The trepanning laser beam drilling is repeated any one of a number of times depending upon the particular numbers of openings 120 to be formed.

Figure 6:
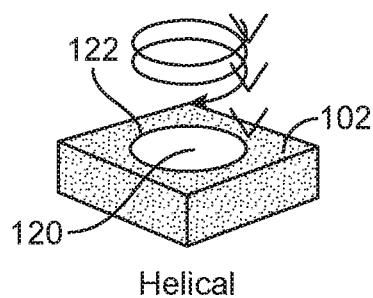
FIG. 6 is a perspective view of the formation of an opening using a helical laser in accordance with one embodiment.

FIG. 6 is a perspective view of the formation of opening 120 using a helical laser in accordance with one embodiment. In accordance with this embodiment, a continuous laser shot is moved, e.g., in an overlapping circle, at graft material 102 to form opening 120. For example, the laser is moved in a circular orbit around circumference 122 to form a single opening 120. The circular orbit of the laser is sometimes called helical laser beam drilling. The helical laser beam drilling is repeated any one of a number of times depending upon the particular numbers of openings 120 to be formed.

In one embodiment, once laser cauterized openings 120 have been introduced into graft material 102 in accordance with any one of the embodiments discussed above, a bioabsorbable material is then used to fill the openings 120 in graft material 102 as discussed below.

Figure 7A:
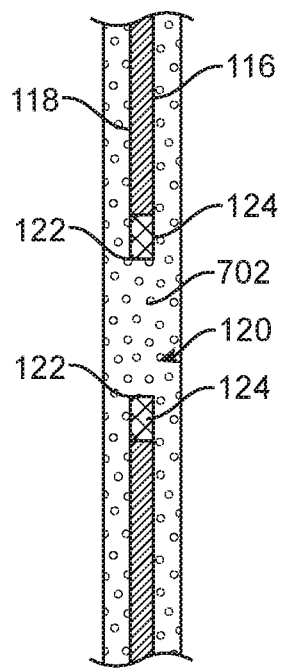
FIG. 7A is a cross-sectional view of an opening along the line VII-VII of FIG. 2 in accordance with one embodiment.

FIG. 7A is a cross-sectional view of opening 120 along the line VII-VII of FIG. 2 in accordance with one embodiment. In accordance with this embodiment, a bioactive material 702 fills openings 120. Bioactive material 702 is applied as a layer to cover outer surface 118, inner surface 116, or both outer surface 118 and inner surface 116 of graft material 102. Bioactive material 702 can be applied to the entire area of graft material 102. However, in another embodiment, bioactive material 702 is applied to selective zones of graft material 102, e.g., to the areas where openings 120 are created only.

Figure 7B:
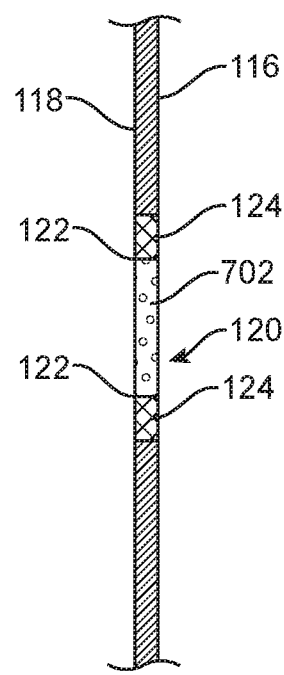
FIG. 7B is a cross-sectional view of the opening along the line VII-VII of FIG. 2 in accordance with another embodiment.

FIG. 7B is a cross-sectional view of opening 120 along the line VII-VII of FIG. 2 in accordance with another embodiment. In accordance with this embodiment, bioactive material 702 fills openings 120. Bioactive material 702 is a plug that fills opening 120 without extending onto outer surface 118 and/or inner surface 116 of graft material 102. In light of this disclosure, those of skill in the art will understand that bioactive material 702 may not be entirely contained within openings 120 and some bioactive material 702 may overlap onto outer surface 118 and/or inner surface 116 of graft material 102 in one embodiment.

Referring now to FIGS. 7A and 7B together, by filling openings 120, bioactive material 702 reinforces the mechanical properties of graft material 102. Bioactive material 702 enables acute resistance to type IV endoleaks, i.e., leaks through graft material 102. Furthermore, in one embodiment, bioactive material 702 degrades on a biological timescale that matches and promotes the speed of tissue in growth. As the tissue grows into openings 120 and replaces bioactive material 702, type IV endoleaks are prevented and migration resistance of stent-graft 100 is improved. Generally, the structure of openings 120 along with bioactive material 702 allows for the recruitment and proliferation of cells and for neovascularization to occur.

Further, in one embodiment, bioactive material 702 is a tissue healing promoting material that serves to promote the healing process, e.g., the recruitment and proliferation of cells that drive the healing process. Examples of bioactive material 702 include polymer polyglycolic-lactic acid (PGLA), and poly(glycerol sebacate) (PGS).

Bioactive material 702 is applied using any one of a number of techniques in accordance with various embodiments. For example, bioactive material 702 is applied by spraying, coating, and/or brushing. In one embodiment, bioactive material 702 is vacuum applied, i.e., a vacuum is formed within graft material 102 which draws (sucks) bioactive material 702 into openings 120. In yet another embodiment, bioactive material 702 is applied by electro spinning, i.e., using electric force to draw bioactive material 702 into openings 120. Although a few examples are provided, bioactive material 702 can be applied in a variety of different techniques in accordance with different embodiments.

Referring again to FIG. 1, in accordance with one embodiment, openings 120 are formed within graft material 102 at or adjacent proximal end 108 of graft material 102. The region 126 of graft material 102 in which openings 120 are formed is referred to as a permeable zone 126 of graft material 102. The region 128 of graft material 102 which as an absence of openings 120, sometimes called native graft material 102, is referred to as a non-permeable zone 128 of graft material 102. Permeable zone 126 extends distally from proximal end 108 to non-permeable zone 128. Non-permeable zone 128 extends distally from permeable zone 126 to distal end 112.

Figure 8:
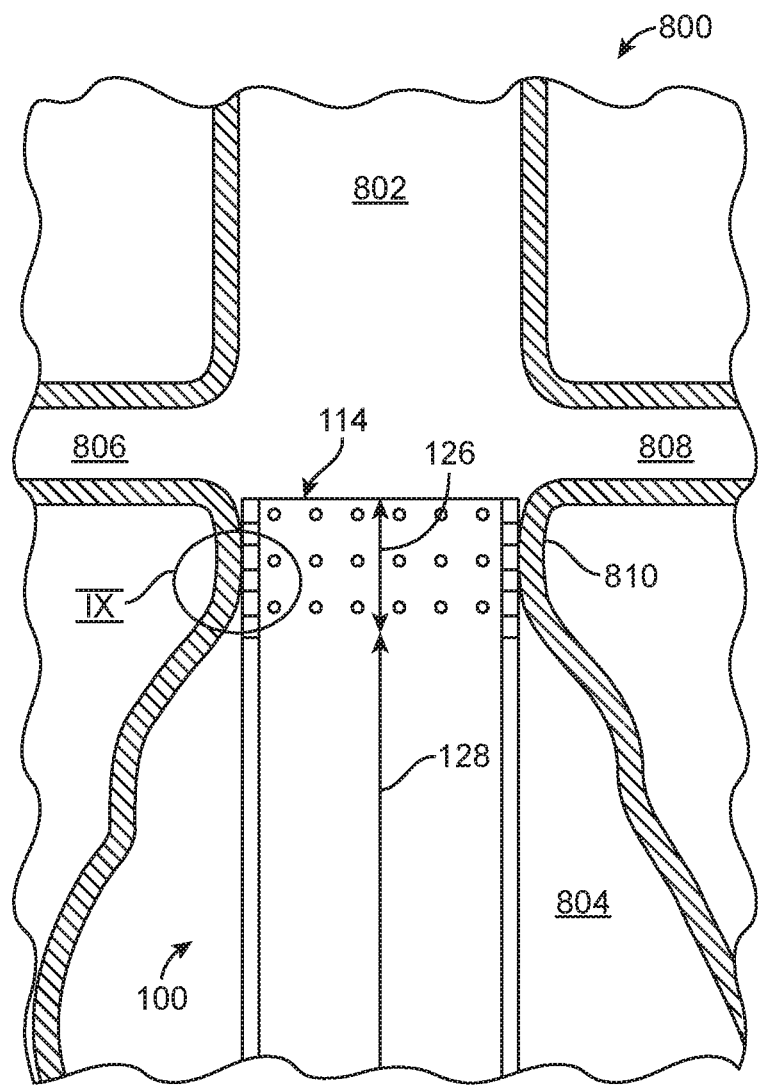
FIG. 8 is a cross-sectional view of a vessel assembly including the stent-graft of FIGS. 1 and 2 in accordance with one embodiment.

FIG. 8 is a cross-sectional view of a vessel assembly 800 including stent-graft 100 of FIGS. 1 and 2 in accordance with one embodiment. Referring now to FIG. 8, a vessel 802, e.g., the aorta, includes an aneurysm 804. Stent-graft 100 is deployed into vessel 802 to exclude aneurysm 804 using any one of a number of techniques well known to those of skill in the art.

Emanating from vessel 802 is a first branch vessel 806 and a second branch vessel 808, sometimes called visceral branches of the abdominal aorta. The location of branch vessels 806, 808 vary from patient to patient. Examples of branch vessels include the renal arteries (RA) and the superior mesenteric artery (SMA).

Stent-graft 100 is deployed just distal of branch vessels 806, 808. Permeable zone 126 is deployed in the landing zone 810 between branch vessels 806, 808 and aneurysm 804. Over time, tissue from vessel 802 will become integrated with openings 120 and more generally within graft material 102 thus preventing leakage around permeable zone 126 and migration of stent-graft 100 as described below in reference to FIGS. 9 and 10.

Figure 9:
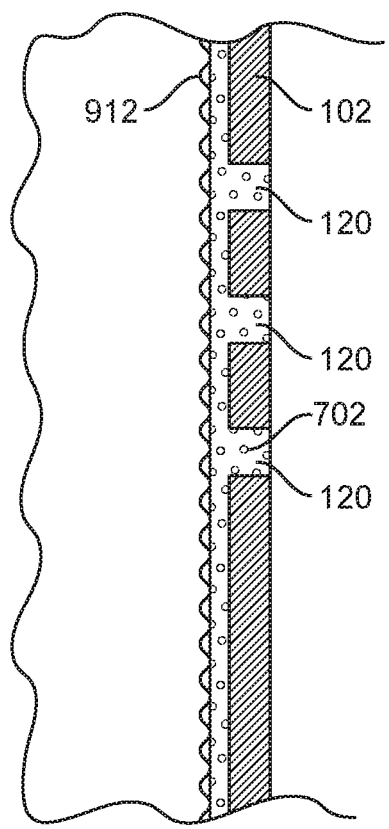
FIG. 9 is an enlarged cross-sectional view of a region IX of FIG. 8 just after initial deployment of the stent-graft in accordance with one embodiment.
Figure 10:
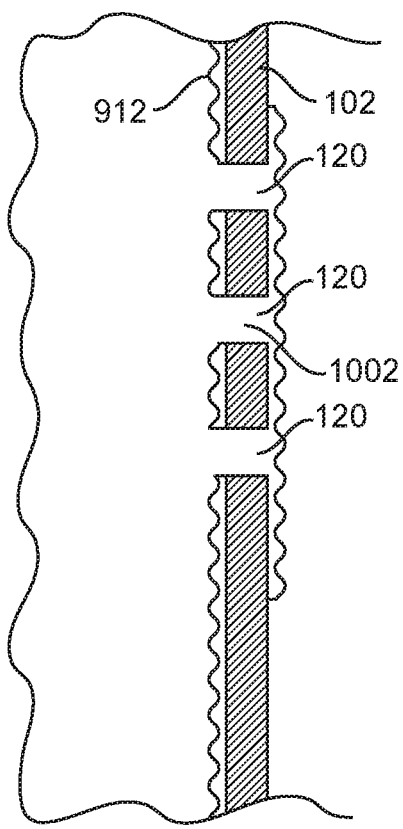
FIG. 10 is an enlarged cross-sectional view of the region IX of FIG. 8 after a period of time after deployment of the stent-graft in accordance with one embodiment.

FIG. 9 is an enlarged cross-sectional view of a region IX of FIG. 8 just after initial deployment of stent-graft 100 in accordance with one embodiment. FIG. 10 is an enlarged cross-sectional view of the region IX of FIG. 8 after a period of time after deployment of stent-graft 100 in accordance with one embodiment.

Referring to FIG. 9, upon deployment of stent-graft 100, permeable zone 126 is in contact with a vessel wall 912 of vessel 802. Bioactive material 702 seals openings 120 in accordance with this embodiment. Over time, bioactive material 702 is replaced with tissue 1002 from vessel wall 912 that integrates within and through openings 120 as illustrated in FIG. 10. Tissue 1002 prevents leakage around permeable zone 126 and migration of stent-graft 100.

Referring again to FIG. 8, once anchored within vessel 802, blood flows through lumen 114 and more generally through stent-graft 100 thus excluding aneurysm 804.

Although a particular example of permeable zone 126 and non-permeable zone 128 are provided, by using a laser to form openings 120, the location of permeable zone 126 and non-permeable zone 128 can be readily modified depending upon the particular application desired as discussed further below in accordance with other embodiments.

More particularly, in accordance with this embodiment, a method to enhance tissue integration through porosity while providing resistance to endoleaks and maintaining sufficient mechanical strength of graft material 102 is provided. This is accomplished by selectively generating precise openings 120, sometimes called ingress channels, using a laser and subsequently filling openings 120 with bioabsorbable material 702.

A feature of utilizing a laser to create openings 120 for tissue integration builds from its tunability. In contrast to control of a weave, a laser in accordance with one embodiment precisely places openings 120 in any pattern and location, and on any textile that forms graft material 102. Further, the power and focus of the laser is precisely adjusted to control the diameter and shape, e.g., conicality, of openings 120. All parameters of openings 120 can be controlled at will, allowing for the opportunity to selectively enhance and optimize the permeability of graft material 102 in a vessel such as vessel 802. Some examples in accordance with various embodiments are provided below.

Figure 11:
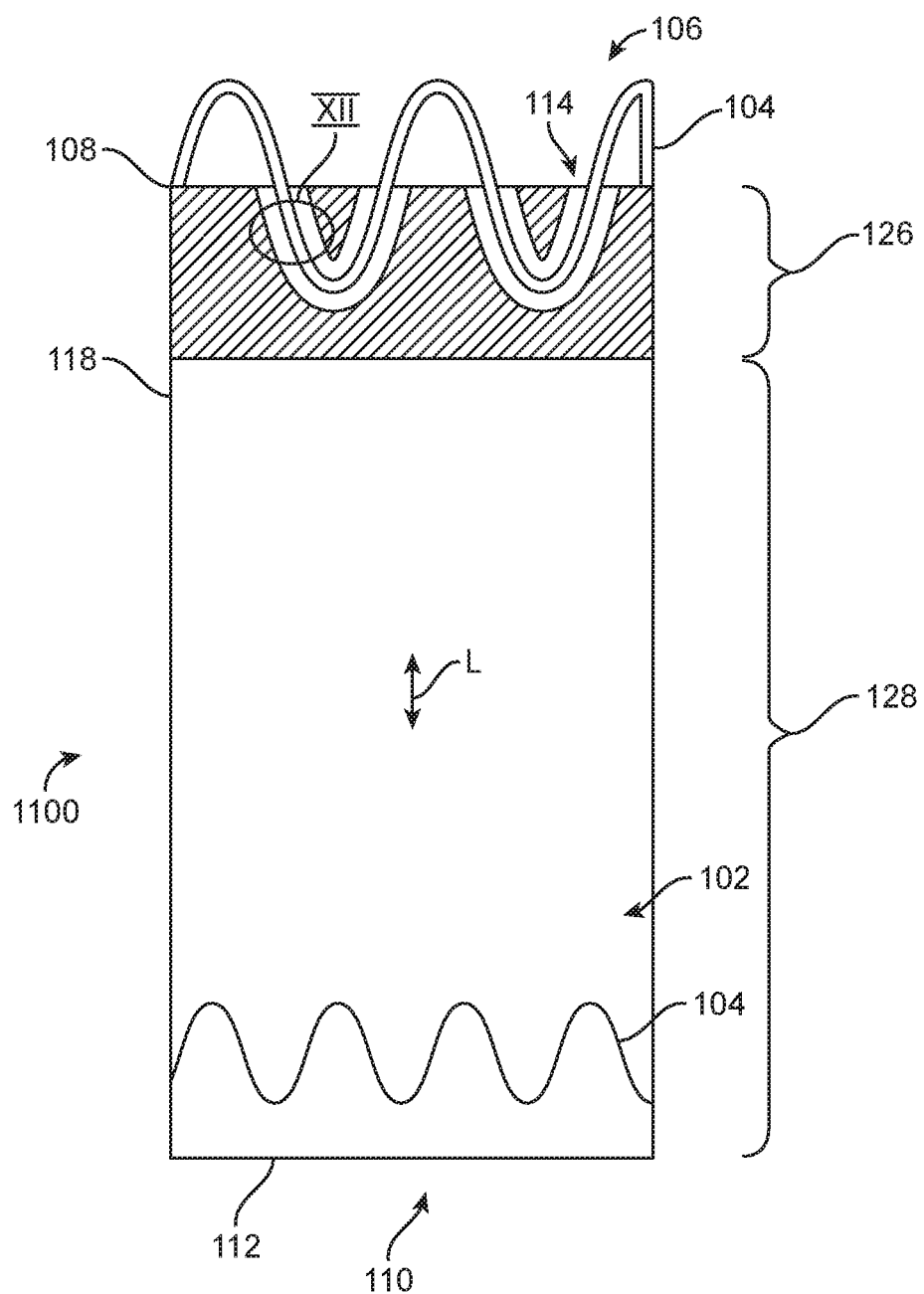
FIG. 11 is a perspective view of an enhanced permeability stent-graft in accordance with another embodiment.
Figure 12A:
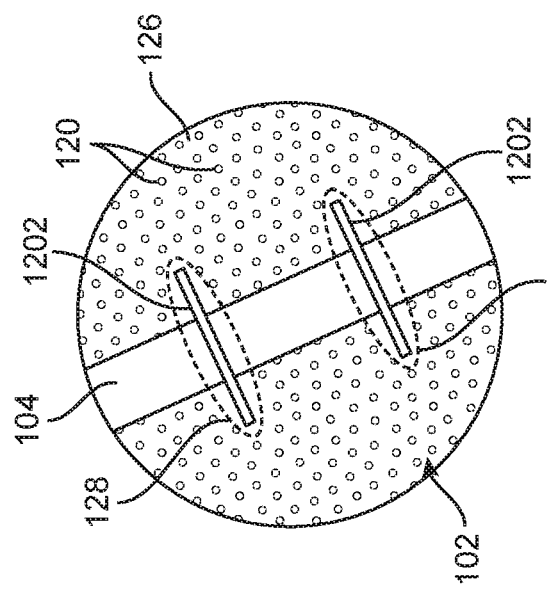
FIG. 12A is an enlarged perspective view of a region XII of the stent-graft of FIG. 11 in accordance with one embodiment.

FIG. 11 is a perspective view of an enhanced permeability stent-graft 1100 in accordance with another embodiment. FIG. 12A is an enlarged perspective view of a region XII of stent-graft 1100 of FIG. 11 in accordance with one embodiment. Stent-graft 1100 of FIG. 11 is similar to stent-graft 100 of FIG. 1 and only the significant differences are discussed below.

Referring now to FIG. 11, permeable zone 126, which includes openings 120, is indicated as a shaded region. As shown in FIG. 12A, permeable zone 126 surrounds stent ring 104 and follows the sinusoidal contour of stent ring 104 but does not overlap with stent ring 104 or sutures 1202 that attach stent ring 104 to graft material 102. In other words, non-permeable zone 128, i.e., graft material 102 without openings 120, overlaps stent ring 104 and sutures 1202.

By forming non-permeable zone 128 to overlap stent ring 104 and sutures 1202, the region of graft material 102 acting in cooperation with stent ring 104 and sutures 1202 has maximized strength, e.g., the strength of graft material 102. This minimizes the possibility of failure of graft material 102 due to the stress placed upon graft material 102 from stent ring 104 and sutures 1202.

Figure 12B:
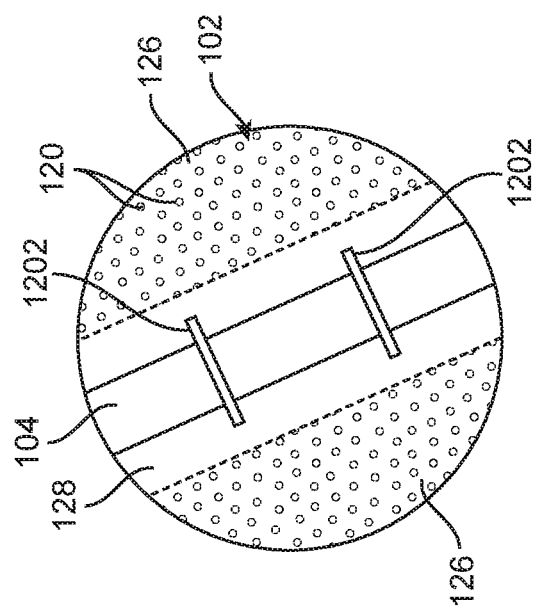
FIG. 12B is an enlarged perspective view of the region XII of the stent-graft of FIG. 11 in accordance with another embodiment.

FIG. 12B is an enlarged perspective view of region XII of stent-graft 1100 of FIG. 11 in accordance with another embodiment. As shown in FIG. 12B, permeable zone 126 overlaps with stent ring 104 but does not overlap with sutures 1202. Oval non-permeable zones 128, i.e., graft material 102 without openings 120, overlap sutures 1202. More particularly, only non-permeable zones 128 and stent ring 104 overlap sutures 1202. By forming non-permeable zones 128 to overlap sutures 1202, sutures 1202 are stitched into regions of graft material 102 with maximized strength. This minimizes the possibility of failure of graft material 102 due to the stress placed upon graft material 102 from sutures 1202.

Figure 13:
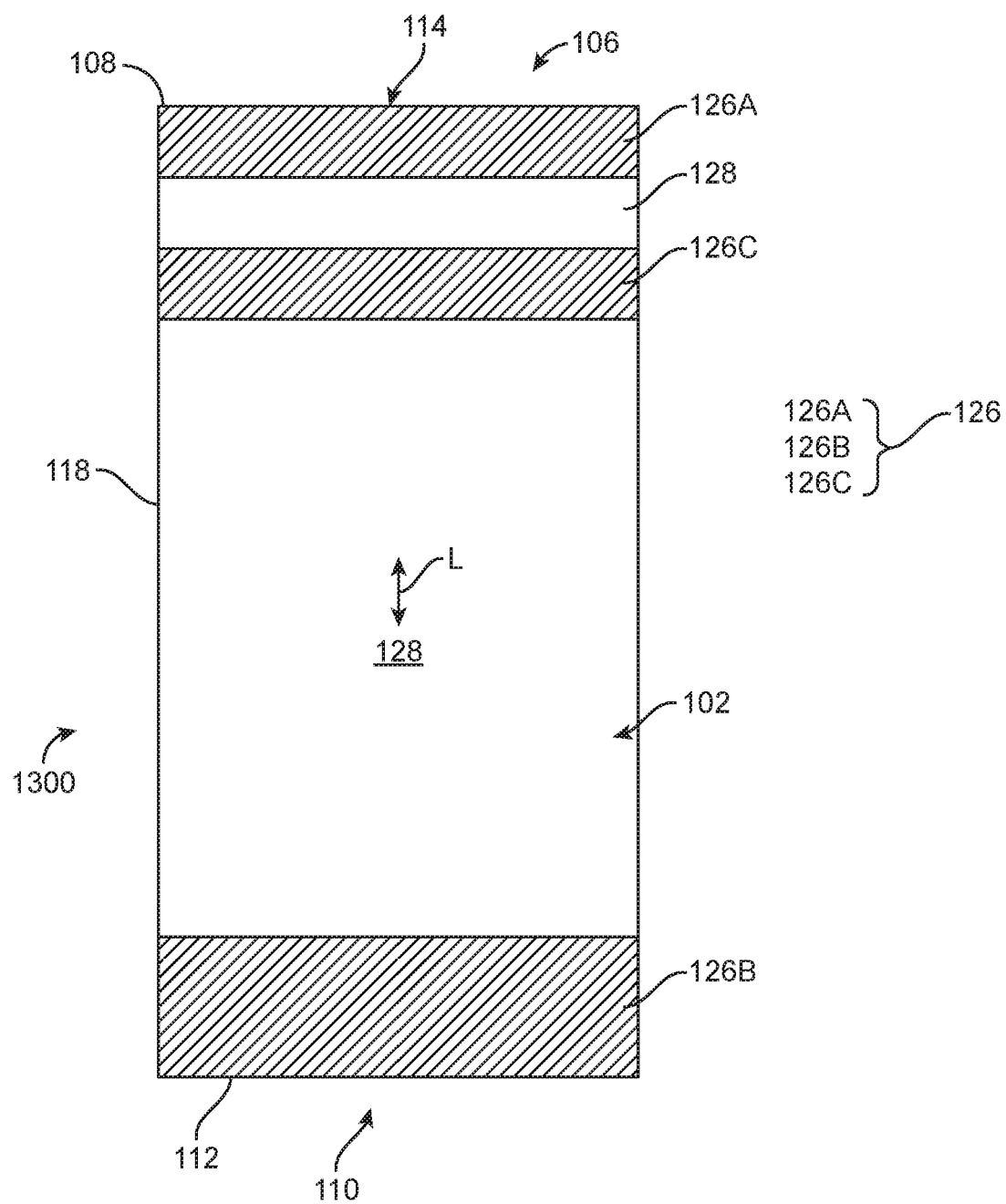
FIG. 13 is a perspective view of an enhanced permeability stent-graft in accordance with another embodiment.

FIG. 13 is a perspective view of an enhanced permeability stent-graft 1300 in accordance with another embodiment. Stent-graft 1300 of FIG. 13 is similar to stent-graft 100 of FIG. 1 and only the significant differences are discussed below. In FIG. 13, stent rings 104 as illustrated in FIG. 1 are not illustrated for simplicity although stent-graft 1300 includes stent rings 104 in other embodiments.

Referring now to FIG. 13, permeable zone 126 is formed as one or more discrete circumferential bands (regions or rings) around graft material 102. In accordance with this embodiment, permeable zone 126 includes three discrete circumferential permeable zones 126A, 126B, 126C. For example, a proximal permeable zone 126A is formed at proximal end 108 and a distal permeable zone 126B is formed at distal end 112 of graft material 102. Illustratively, proximal permeable zone 126A and a distal permeable zone 126B enhance tissue integration at both proximal and distal ends 108, 112 of graft material 102.

In accordance with this embodiment, a middle permeable zone 126C is formed separated from but between bands 126A, 126B. Non-permeable zones 128, which are also shaped as circumferential bands, are located between and separate permeable zones 126A, 126B, 126C to maintain the strength of stent-graft 1300. Although a particular arrangement of permeable zones 126A, 126B, 126C are illustrated and discussed, generally, one or more circumferential permeable zones are formed.

Figure 14:
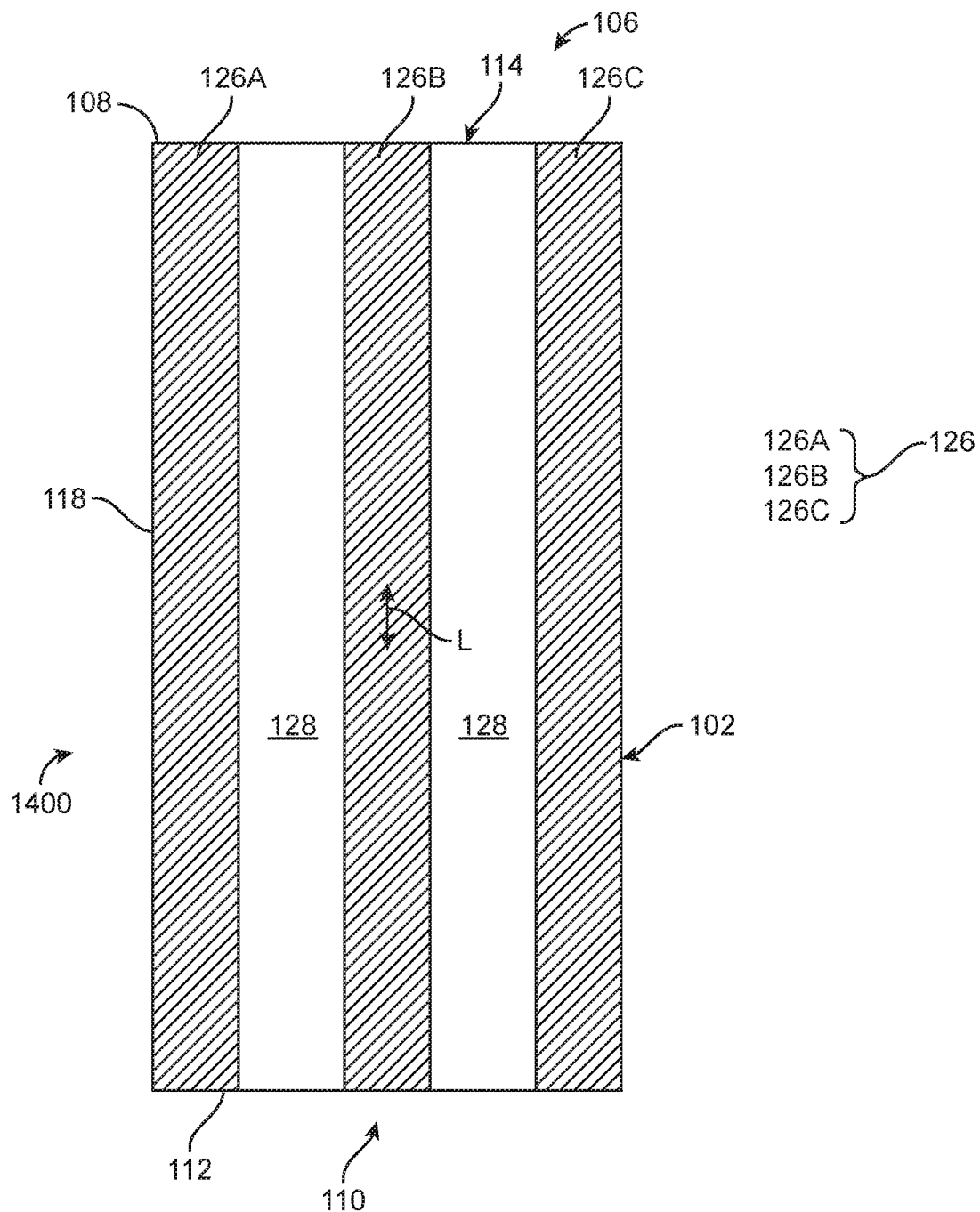
FIG. 14 is a perspective view of an enhanced permeability stent-graft in accordance with yet another embodiment.

FIG. 14 is a perspective view of an enhanced permeability stent-graft 1400 in accordance with yet another embodiment. Stent-graft 1400 of FIG. 14 is similar to stent-graft 100 of FIG. 1 and only the significant differences are discussed below. In FIG. 14, stent rings 104 as illustrated in FIG. 1 are not illustrated for simplicity although stent-graft 1400 includes stent rings 104 in other embodiments.

Referring now to FIG. 14, permeable zone 126 is formed as one or more discrete longitudinal strips (regions) extending along the length of graft material 102 generally parallel to longitudinal axis L. For example, permeable zone 126 includes a plurality of discrete longitudinal permeable zones 126A, 126B, 126C although there may be additional longitudinal permeable zones not visible in the view of FIG. 14, e.g., on the backside of stent-graft 1400. For example, each permeable zone 126A, 126B, 126C is formed extending the entire length from proximal end 108 to distal end 112 of graft material 102. Illustratively, permeable zones 126A, 126B, 126C enhance tissue integration along the entire length of graft material 102.

Non-permeable zones 128, which are also shaped as longitudinal strips, are located between and separate permeable zones 126A, 126B, 126C to maintain the strength of stent-graft 1400. Although a particular arrangement of permeable zones 126A, 126B, 126C are illustrated and discussed, generally, one or more longitudinal permeable zones 126A, 126B, 126C are formed. Further, the length of permeable zones 126A, 126B, 126C vary in other embodiments, e.g., do not extend the entire length of stent-graft 1400.

Figure 15:
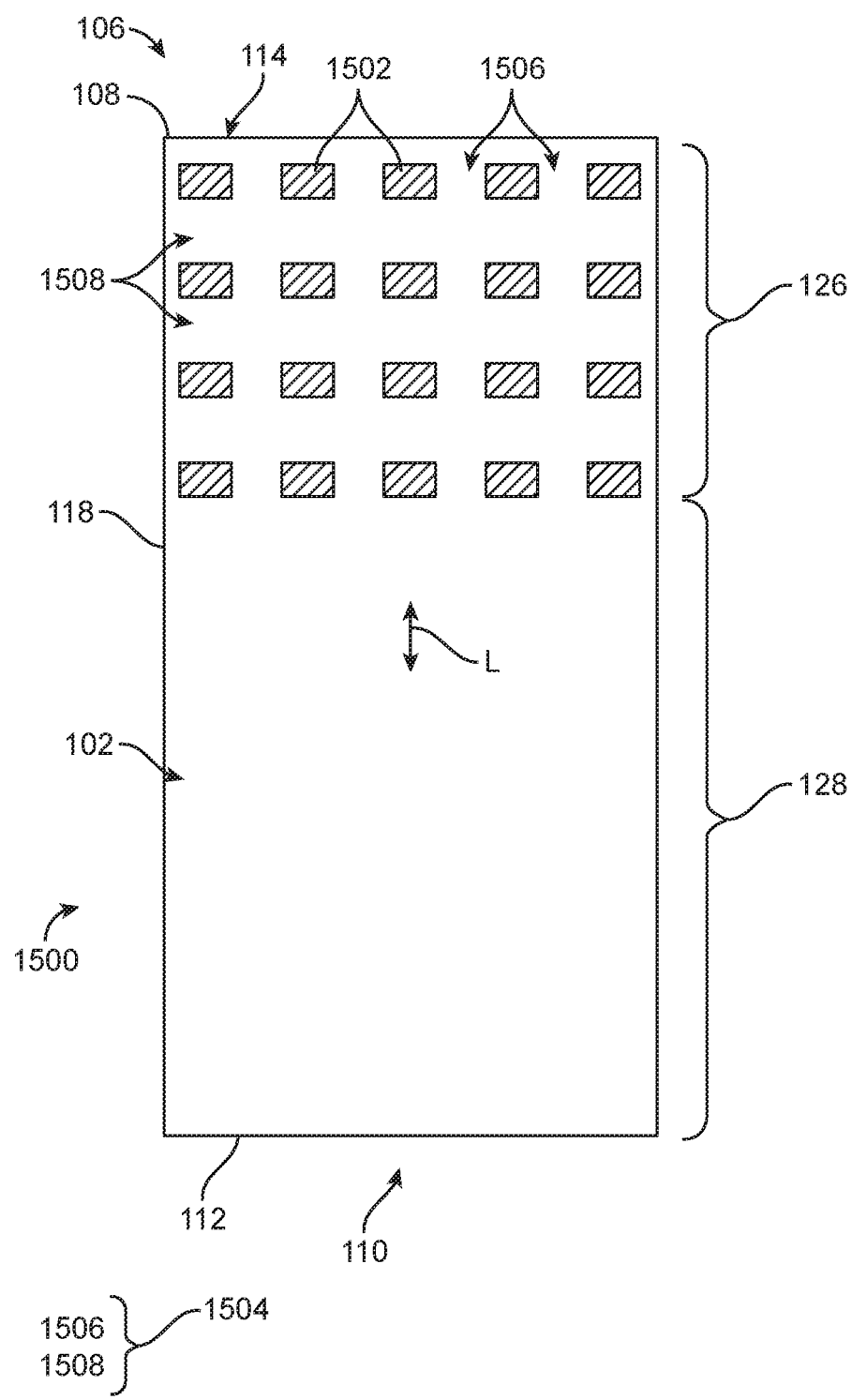
FIG. 15 is a perspective view of an enhanced permeability stent-graft in accordance with yet another embodiment.

FIG. 15 is a perspective view of an enhanced permeability stent-graft 1500 in accordance with yet another embodiment. Stent-graft 1500 of FIG. 15 is similar to stent-graft 100 of FIG. 1 and only the significant differences are discussed below. In FIG. 15, stent rings 104 as illustrated in FIG. 1 are not illustrated for simplicity although stent-graft 1500 includes stent rings 104 in other embodiments.

Referring now to FIG. 15, permeable zone 126 is formed as one or more discrete areas (regions). For example, permeable zone 126 includes a plurality of discrete permeable zones 1502 adjacent proximal end 108. For example, each permeable zone 1502 is formed as a rectangle. Illustratively, each permeable zone 126 includes one hundred openings 120, each opening 120 having a diameter of 50 microns (μm).

Permeable zones 1502 are arranged in columns, e.g., longitudinally and in rows, e.g., circumferentially. Illustratively, permeable zones 1502 define a non-permeable array 1504, e.g., in a checkerboard shape. Non-permeable array 1504 includes non-permeable longitudinal strips 1506 intersecting non-permeable circumferential bands 1508.

Non-permeable array 1504 is between and separates permeable zones 1502 to maintain the strength of stent-graft 1500 while permeable zones 1502 enhances tissue integrations. Although a particular arrangement of permeable zones 1502 is illustrated and discussed, permeable zones 1502 are formed in different arrangements in different embodiments. For example, diagonal uncut regions are created in another embodiment. In yet another embodiment, a cut pattern which has circumferential, longitudinal and/or diagonal lines are created, e.g., which match the original textile mechanical properties while still providing regions for tissue ingrowth.

Figure 16:
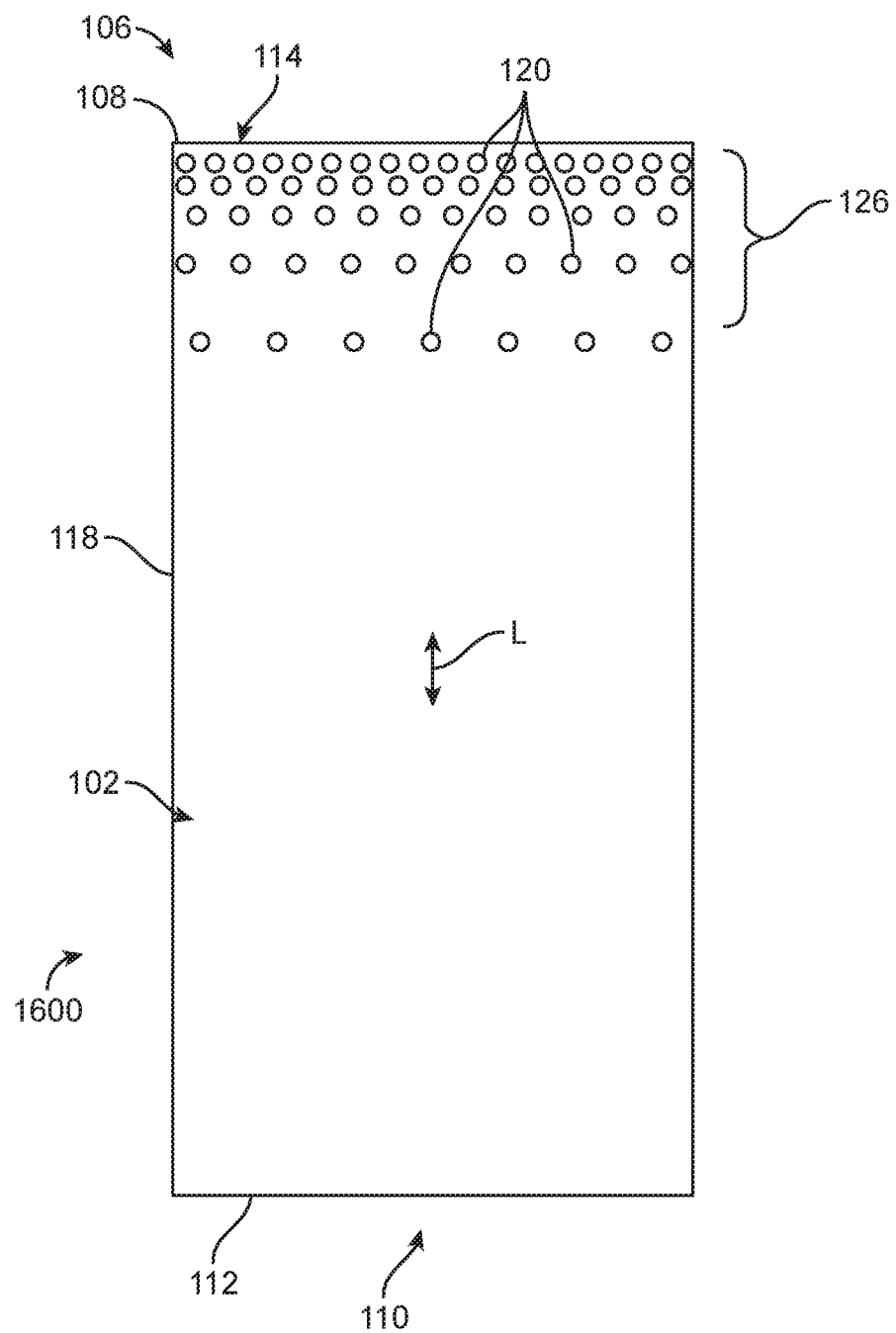
FIG. 16 is a perspective view of an enhanced permeability stent-graft in accordance with yet another embodiment.

FIG. 16 is a perspective view of an enhanced permeability stent-graft 1600 in accordance with yet another embodiment. Stent-graft 1600 of FIG. 16 is similar to stent-graft 100 of FIG. 1 and only the significant differences are discussed below. In FIG. 16, stent rings 104 as illustrated in FIG. 1 are not illustrated for simplicity although stent-graft 1600 includes stent rings 104 in other embodiments.

Referring now to FIG. 16, permeable zone 126 is formed with a varying density of openings 120, e.g., a varying number of openings 120 per given area of graft material 102.

For example, the density of openings 120 is greatest at proximal end 108 and decreases linear as the distance from proximal end 108 increases.

Illustratively, the density is greatest at proximal end 108 to maximize tissue integration at proximal end 108. Then as the distance from proximal end 108 increase, less tissue integration occurs while the strength of graft material 102 increases due to the decreasing density of openings 120. For example, the density is greatest in the seal zone and then the density tapers out towards regions which will be interfacing with the aneurysm sac. Although a particular arrangement of density variation of openings 120 is illustrated and discussed, permeable zone 126 is formed with different density arrangements in different embodiments depending upon the particular application.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A prosthesis comprising:
   a graft material comprising a permeable zone and oval non-permeable zones, wherein:
   the permeable zone comprises laser-created openings; and
   the non-permeable zones have an absence of the openings; and
   a stent ring coupled to the graft material by sutures, only the non-permeable zones and the stent ring overlapping the sutures, the permeable zone overlapping the stent ring.

2. The prosthesis of claim 1 wherein the permeable zone comprises at least one circumferential permeable zone.

3. The prosthesis of claim 1 wherein the permeable zone comprises at least one longitudinal permeable zone.

4. The prosthesis of claim 1 wherein the permeable zone comprises a varying density of the openings.

5. The prosthesis of claim 1 wherein the graft material comprises an inner surface and an outer surface;
   the openings extending through the graft material between the inner surface and the outer surface, each opening being surrounded by a fused region of the graft material.

6. The prosthesis of claim 5 wherein the fused region is an area of the graft material that is fused together.

7. The prosthesis of claim 5 wherein the graft material comprises filaments, the filaments being bonded together in the fused region.

8. The prosthesis of claim 5 wherein the fused region is a continuous strip extending outward from and surrounding the openings.

9. The prosthesis of claim 5 wherein the openings are circular and are defined by a circumference, the circumference being an edge of the graft material, wherein the fused region is an annulus extending outward of the openings from the circumference.

10. The prosthesis of claim 5 further comprising a bioactive material within the openings.

11. The prosthesis of claim 10 wherein the bioactive material is on the outer surface of the graft material.

12. A prosthesis comprising:
    a graft material comprising a permeable zone and a non-permeable zone wherein:
    the permeable zone comprises laser-created openings; and
    the non-permeable zone has an absence of the openings; and
    a sinusoidal stent ring coupled to the graft material by sutures, only the non-permeable zone overlapping the stent ring and sutures, wherein the permeable zone surrounds the stent ring and follows a sinusoidal contour of the sinusoidal stent ring.

* * * * *